United States Patent [19]
Jacobsen et al.

[11] Patent Number: 5,782,799
[45] Date of Patent: Jul. 21, 1998

[54] METHOD FOR AUTOMATIC DOSING OF DRUGS

[75] Inventors: Stephen C. Jacobsen; Gaylen M. Zentner, both of Salt Lake City, Utah

[73] Assignee: Sarcos, Inc., Salt Lake City, Utah

[21] Appl. No.: 797,296

[22] Filed: Feb. 7, 1997

[51] Int. Cl.$^6$ .................................................. A61M 31/00
[52] U.S. Cl. ........................ 604/49; 604/131; 604/891.1
[58] Field of Search ............................ 604/49, 65–67, 604/20–23, 890.1, 891.1, 19, 131, 140, 93

[56] References Cited

U.S. PATENT DOCUMENTS

| | | |
|---|---|---|
| 3,840,009 | 10/1974 | Michaels et al. |
| 4,312,347 | 1/1982 | Magoon et al. |
| 4,326,522 | 4/1982 | Guerrero et al. |
| 4,425,117 | 1/1984 | Hugemann et al. |
| 4,439,197 | 3/1984 | Honda et al. |
| 4,457,752 | 7/1984 | Vadasz |
| 4,564,363 | 1/1986 | Bagnall et al. |
| 4,654,363 | 3/1987 | Prugh |
| 5,167,625 | 12/1992 | Jacobsen et al. |
| 5,196,002 | 3/1993 | Hanvoer et al. |
| 5,468,222 | 11/1995 | Altchuler ........................... 604/49 |
| 5,536,247 | 7/1996 | Thornton ........................... 604/49 |
| 5,603,694 | 2/1997 | Brown et al. ...................... 604/49 |
| 5,630,808 | 5/1997 | Magruder et al. ................ 604/892.1 |

*Primary Examiner*—John D. Yasko
*Attorney, Agent, or Firm*—Thorpe North & Western LLP

[57] ABSTRACT

The method for automatic dosing of drugs utilizes a microdelivery device which may be implanted in or otherwise administered to an animal or human. A microdelivery device is configured to have a plurality of compartments, each containing at least one drug so that a plurality of doses of the drug(s) are held within the device. In accordance with the present invention, the microdelivery device selectively actuates the compartments to selectively release doses of the drug(s) to provide an efficacious dosing pattern. One primary function of the present invention is to release two or more pesticides in such a pattern that parasites are effectively controlled while preventing the development of tolerance to the drugs within the parasites. Preferably, the microdelivery device is programmable to effectuate the release of the drug(s) at a desired time to maintain efficacious levels of the drug while minimizing the amount of drug which must be used.

53 Claims, 8 Drawing Sheets

METHOD FOR AUTOMATIC DOSING OF DRUGS

BACKGROUND OF THE INVENTION

1. Field of the Invention

The present invention relates to a method of automatic dosing of drugs. More particularly, the present invention relates to a method for using electromechanical mechanisms and micromachines for dosing of drugs to maximize the effectiveness of the drugs and to prevent the development of drug tolerance and resistance.

2. State of the Art

It is well known in the fields of animal husbandry and veterinary medicine that it is usually desirable and often necessary to treat farm animals with drugs for parasites. The parasites of concern will often vary depending on the farm animal concerned and may include both ectoparasites and endoparasites. To eliminate or control these parasites, farm animals are often sprayed with or fed parasiticides, injected with these drugs or sprayed with drugs which act as parasite repellents. To accomplish such control of the parasites, the farm animals typically must be rounded up and placed in a holding area so that each animal may be properly dosed with the drug(s). Once treated, the animal is released until the next dosing is required.

Unfortunately, rounding up the animals each month, etc., is time consuming and expensive. The animal must be located and then brought to a suitable location for administration of the drug. Because of the time and expense involved with such round-ups, the farmer is forced into a compromise of overdosing the animal with a very large dose of the drug to prolong the period during which the drug is present at levels which meet or exceed the minimum effective level, thereby decrease the frequency with which the drugs must be administered, or accepting the expense of frequent round-ups to repetitively doses the animals. For example, a topically applied drug may have an efficacy threshold which relates to a 750 milligram dose of a given medication. However, to extend the period between dosing, a significantly larger dose is typically used. In FIG. 1, there is shown a curve indicating a normal, exponentially declining (i.e., first-order) efficacy curve where the drug is provided by prior art diffusion devices, such as ear tags, at a very high initial dose in order to maintain drug levels above the efficacy threshold for a prolonged period.

Referring to FIG. 1, the initially high drug level 10 that is available early in the treatment period is typically much higher than the efficacy threshold 20. In the present example, the initially high drug level 10, is 3,750 milligrams, a drug level that would require a dose which is at least four to five times higher than the efficacy threshold for the drug used. Such large doses create several problems and negatively impact the animal by causing host toxicity, decreased weight gains, and loss of income to the animal handlers/owners.

An additional problem with the initial high dose is that high levels of the drug may still be present should the farmer desire to slaughter the animal within the time period correlated with the upper portion, indicated at 30, of the first-order declining kinetic curve. The high, persistent drug levels can limit the farmer's marketing response and potentially lead to adverse reactions in consumers.

In the FIG. 1 example, the drug, assumed to be a parasiticide for discussion purposes, which has been diffused onto/into the animal remains above the efficacy threshold for approximately 90 days. Once the amount of drug present falls below the efficacy threshold, the drug is present in insufficient amounts to adequately kill the targeted parasites. However, it is well known that the prolonged presence of subtherapeutic levels of a drug gives rise to the development of resistance to the drug within the targeted parasites. In a resistant parasite population, the efficacy threshold is shifted upward substantially. Therefore, due to use of prior art diffusion controlled dosage forms, numerous previously beneficial antibiotics and parasiticides are now of limited effectiveness because the target microbes and parasites have developed sufficient resistance to the drug to withstand even very high dosages that the host animal cannot tolerate. Drugs that are not biocides also are negatively impacted by this type of dosing pattern as manifested by enzyme down regulation and the clinical development of tachyphylaxis.

There have been numerous attempts to overcome these concerns. For example, it has been proposed to implant in farm animals devices which provide for the release of drugs at a time other than implantation. Examples of such devices are included in the U.S. Pat. Nos. 4,564,363, 4,326,522, 4,425,117, 4,439,197, 3,840,009, 4,312,347 and 4,457,752. Unfortunately, these devices tend to be expensive to use, typically they allow only for a one time (continuous) discharge of a single drug, and are otherwise disadvantageous. Thus, there is a need for a method of administering drugs which overcomes the disadvantages of the prior art.

SUMMARY OF THE INVENTION

It is an object of the present invention to provide an improved method for dosing animals which requires only a single application to the animal during a treatment period.

It is another object of the present invention to provide such a method which prevents or substantially reduces the development of drug resistance within the targeted parasite or microbe.

It is still another object of the present invention to provide a method which maintains an efficacious dose of the drug within the animal throughout the treatment period.

It is yet another object of the present invention to minimize the amount of drug necessary to stay above the drug's efficacy threshold by providing dosing events which are accurate and precise.

It is still yet another object of the present invention to enable the user to control the amount of the drug present in the animal's system to thereby enable the user to increase drug levels during traditionally high periods of parasite infestation.

Yet another object of the present invention is to provide such a method which provides electronic control over drug delivery, rather than depending on the chemical attributes of the drug being delivered.

Still yet another object of the present invention is to provide such a method which is independent of the drug.

Additional objects of the invention include the use of devices which may be used topically, ruminally or implanted, and which may be used in both human and animal applications.

The above and other objects not specifically enumerated are realized in specific illustrated embodiments of a method for automatic repetitive dosing of a single drug or alternate dosing of two or more drugs including a microdelivery system which has at least two containers for holding at least a first drug and a second drug to be dosed and which is attached to, implanted in, or orally administered to the animal. The microdelivery system is programmed to release an initial dose of the first drug to the animal. The initial dose is then followed by periodic doses of the first or second drugs to achieve an efficacious treatment of the animal.

In accordance with one aspect of the invention, the first dose is administered to the animal and the amount of drug is allowed to diminish in, for example, a first-order kinetic decline. Of course, those skilled in the art will appreciate that the present invention applies equally wells to any type of decreasing drug concentration.

Before the first drug is allowed to pass below the known efficacy threshold for the first drug, the microdelivery system releases another dose of the first drug, or an initial dose of the second drug is administered which is sufficient to bring the amount of the second drug in/on the animal above the efficacy threshold for the second drug. The dosing of the first and second drugs are then cycled to achieve a desired efficacy by always maintaining at least one of the drugs at levels above the efficacy threshold for that drug. This repetitive dosing approach maintains high-level efficacy with a minimum drug exposure for the host animal and the environment. For example, the first and second drugs may be administered shortly before the other drug drops below the efficacy threshold, or several doses of the first drug may be provided with an occasional dose of the second drug, or several doses only of the first drug may be provided.

In accordance with another aspect of the present invention, the first and second drugs are delivered in such a manner that each drug remains present in the body in amounts above the efficacy threshold, or, the two drugs may be alternated to ensure that at least one of the drugs is always well above the efficacy threshold without introducing excessive amounts of either drug into the animal.

In accordance with yet another aspect of the present invention, the microdelivery system could be used to supply a plurality of different drugs with any desired sequence and timing during a designated period. Thus, for example, antibiotics or parasiticides could be delivered monthly as described above and other drugs, such as hormones which stimulate animal growth, could also be provided. The use of the microdelivery system allows a farmer to provide all of the medication needs for an animal for a prolonged period of time with a single administration of the programmed microdelivery system. Such a method can save considerable amounts of time and money by avoiding repetitive handling of the animals, avoiding doses which may induce toxicity in the host, and maximizing efficacy with minimal drug doses.

In accordance with still another aspect of the present invention, the amount of drug delivered during each dose may be correlated with the amount of drug required to address particularly high or low infestation patterns. Thus, for example, the amount of drug provided by a dose may be increased or subsequent doses may be delivered more frequently during periods, such as spring or summer, when parasitic infestations may be particularly common, and decreased to a level slightly above the efficacy threshold during fall and winter or other periods when parasite infestations are not as common.

In accordance with still yet another aspect of the invention, a plurality of different drugs for humans and animals may be automatically dosed during different periods. For example, concerns may be present about the use of two drugs because of their proclivity to interact and produce undesirable side effects. With the method of the present invention, a first drug may be delivered and allowed to fall below levels at which it is likely interact with the second drug. The second drug may then be administered and allowed to fall to a sufficiently low level before the first drug is reintroduced. Thus, medical personnel can ensure that a patient has his or her medication administered at appropriate times without requiring the medical personnel to be present each time one of the drugs is administered. Accurate, precise delivery of complex dosing regimens is thus achieved in an unattended and automatic fashion, eliminating patient compliance and practitioner administration errors from the overall therapeutic outcome.

Still another aspect of the invention includes introducing the initial dose of a drug and allowing the drug to diminish, for example, in a first-order kinetic decline. Before the drug is allowed to pass below the efficacy threshold which has been established, the microdelivery system releases a second dose of the drug to maintain the amount of the drug in the patient above the efficacy threshold for the drug.

The microdelivery system is sufficiently small that it may be administered either topically, ruminally, or it may be implanted. If necessary, the dosages provided by the microdelivery system may be maintained within a single compartment for each dose, or larger doses may be achieved by using two or more compartments.

Still yet another aspect of the present invention is mixing two or more drugs within a compartment, or during application to achieve a desired balance of the two drugs which is available to the patient. The two drugs disposed in a single compartment may be selected to interact with each other, or may be simply selected on the basis that dosing of the two drugs is desirable at approximately the same time. When dispensed from separate compartments, the drugs will typically interact in a symbiotic manner to further improve the efficacy of the method of the present invention.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various aspects of the present invention will be described so as to enable one skilled in the art to make and use the invention. It is to be understood that the following description is only exemplary of the principles of the present invention, and should not be viewed as narrowing the pending claims.

Figure 1:
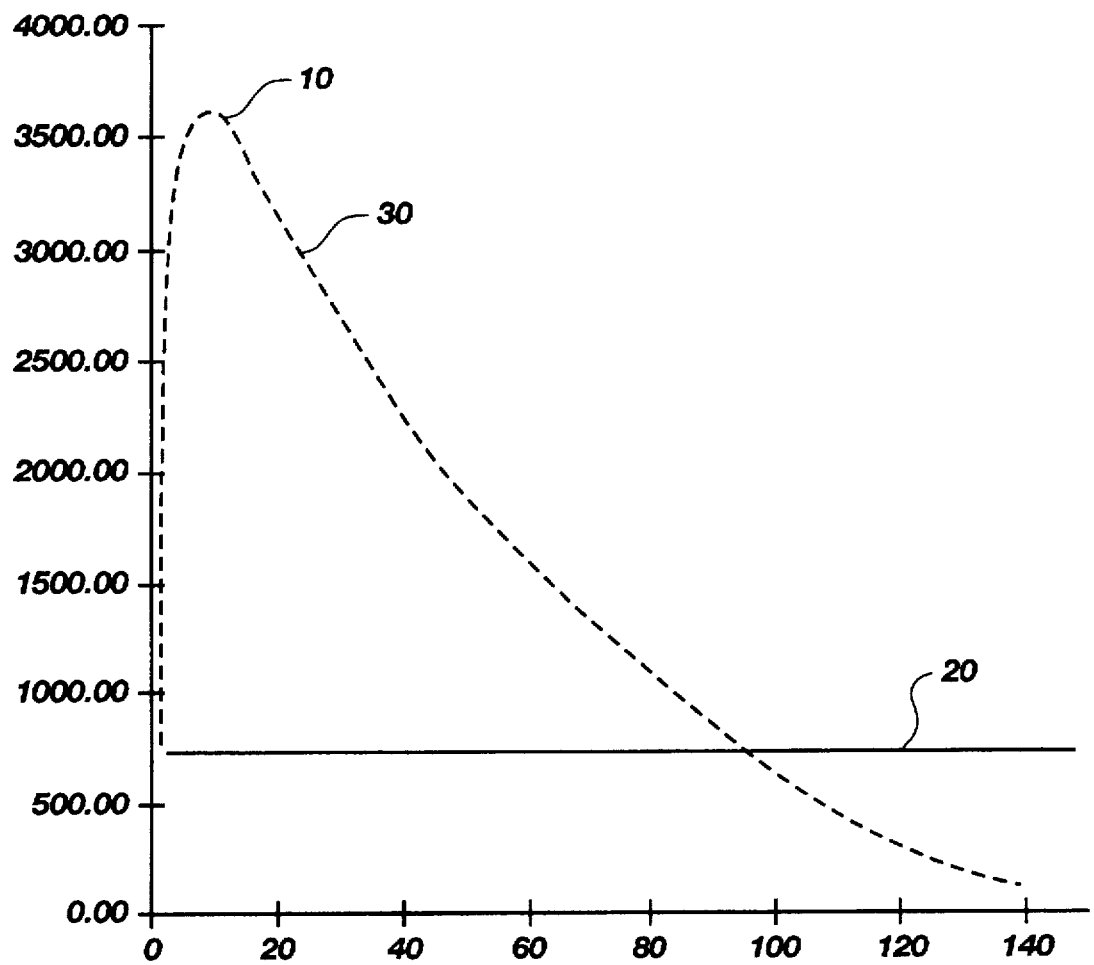
FIG. 1 shows a graph demonstrating a first-order kinetic decline of drug levels in/on an animal when the drug is delivered by a device that releases drug by the conventional diffusion method.
Figure 2A:
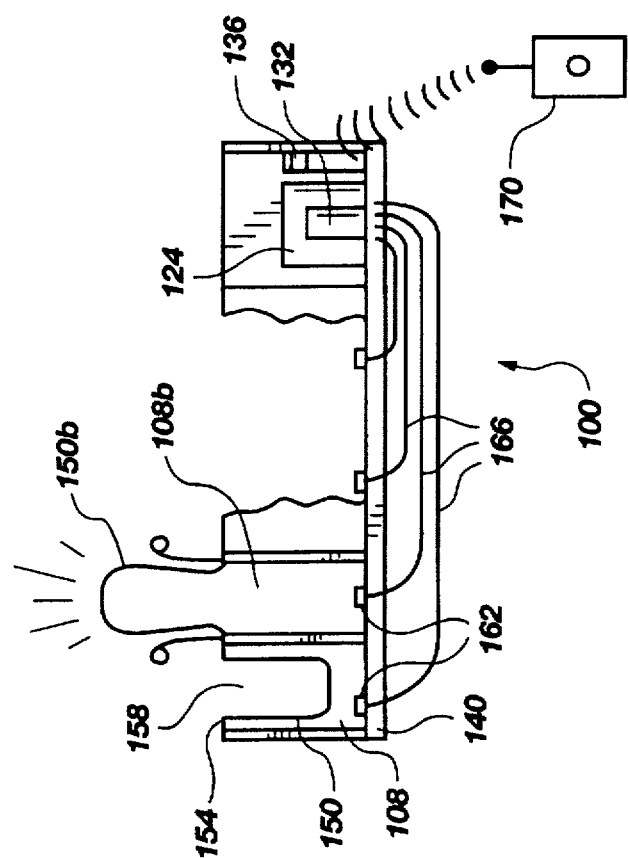
FIG. 2A shows a fragmented, side cross-sectional view of the microdelivery system of FIG. 2.
Figure 2:
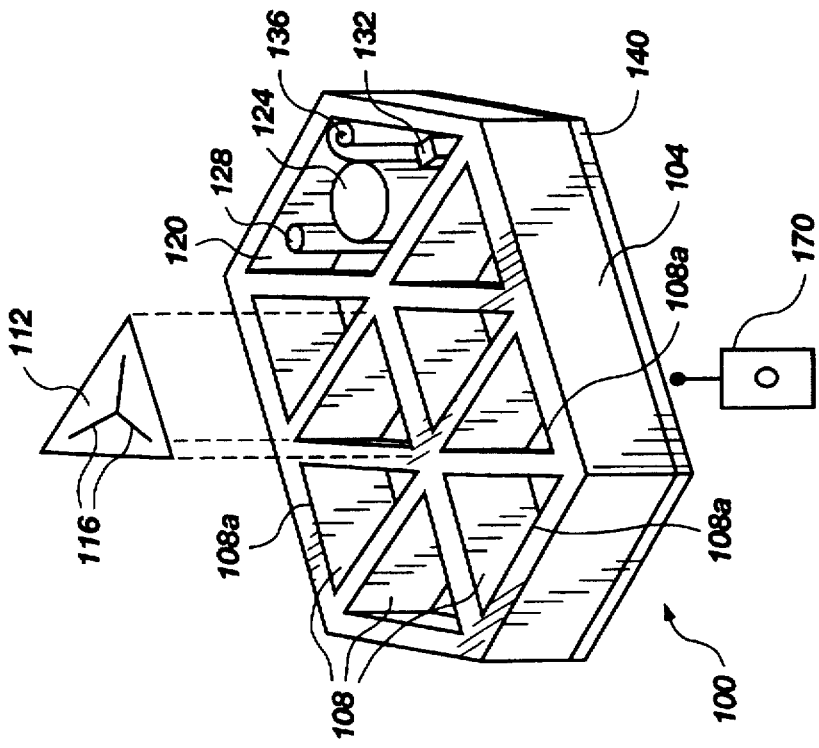
FIG. 2 shows a perspective view of a microdelivery system which may be used to practice the method of the present invention.

Referring to FIGS. 2 and 2A, there is shown a microdelivery system, generally indicated at 100, which may be used to practice the teachings of the present invention. The microdelivery system 100 includes a housing 104 having a plurality of compartments 108 formed therein. Each of the compartments 108 has an open upper end 108a, over which a rupturable or removable cap 112 is placed. The caps 112 may be attached to the housing 104 so that one or two sides rupture when desired, or a plurality of score lines 116 can be made so that the cap 112 opens when forcefully contacted by medication disposed therein.

As shown in FIG. 2, the compartments 108 are arranged in rows to achieve maximum dosing volume in a minimum space. Positioned at one end of the two rows of compartments 108 is a utility compartment 120. The utility compartment 120 is used to house a battery 124, an oscillator 128, and a timing circuit 132. A receiver and antenna 136 may also be provided. The battery 124, the oscillator 128, the timing circuit 132 and the receiver/antenna 136 (if provided) are mounted on a substrate 140 which forms a floor of the utility compartment 120 and the other compartments 108.

Disposed in each compartment 108 is a drug containment sack 150 shown in FIG. 2A. The drug containment sack 150 has an upper opening 154 and a void 158 disposed within the sack 150 for holding medication. The upper opening 154 of each drug containment sack 150 is attached adjacent the opening 108a of a corresponding compartment. The drug containment sacks are provided for holding a drug dose to be delivered to an animal to which the drug delivery system is administered. The drug dose may be formulated as solids such as tablets, powders and granules, semisolids such as ointments and creams, or even solutions, suspensions, and emulsions.

The drug containment sacks will typically be made of material which is flexible and chemically inert. The exact material used to form the sack may vary depending on the drug to be administered. Several likely materials are set forth in U.S. Pat. No. 5,167,625, which is expressly incorporated herein.

Disposed at the bottom of each compartment 108 on the substrate floor 140 is a pyrotechnic gas generating element, typically a bead of material 162 which is responsive to heat resulting from an electrical signal applied to a heating element, thereby igniting and producing gas that fills and pressurizes the corresponding compartment. Alternatively, a non-toxic foam may be produced by an ignition material to similarly fill a corresponding compartment 108. As a compartment 108 fills with gas, the gas forces the corresponding drug containment sack 150 upwardly and the sack, in turn, forces the drug formulation contained therein against the cover 112 which ruptures and allows the drug formulation to be expelled as the sack everts. Sack 150b of FIG. 2A is shown fully everted from compartment 108b which ensures that all drug formulation initially contained in the sack, i.e. a dose, is administered to the patient.

The pyrotechnic gas generating material 162 might illustratively be a composition of nitrocellulose, nitroglycerine, hydrazine, or polyvinyl nitrate. Although not shown, a second or more pyrotechnic gas generating beads might also be included in each compartment to be activated after the first bead has been activated to thereby better ensure the complete release of drug formulation from each compartment.

The oscillator 128 supplies an oscillatory signal to the timing circuit 132 which is adapted to selectively connect the battery 124 to the pyrotechnic gas generating beads 162 in some preferred order (to activate the beads) and with a predetermined delay between activation of the different beads, to thereby discharge and administer doses of drug formulation to the patient (animal or human) over a period of time.

The timing circuit 132 operates in such a manner to selectively and sequentially connect the battery 124 by way of electrical conductors 166 to the pyrotechnic gas generating beads 162. While shown as being disposed underneath the substrate 140, the conductors can also be disposed in or on top of the substrate. Thus, the timing circuit is able to selectively trigger the release of numerous doses of therapeutic drugs over a prolonged period of time. For example, half of the compartments 108 could be filled with a first insecticide and the other half filled with a second insecticide. The timing circuit 132 could be programmed to activate release from a compartment having the first insecticide, and then activate release from a compartment containing the second insecticide after some predetermined delay. If necessary, a dose could be provided by the actuation of two or more compartments.

In such a manner, a single administration of the microdelivery system 100 can deliver a series of medication doses over a prolonged period of time. For example, if a parasiticide were released monthly, a single administration of the microdelivery system 100 would enable treatment of an animal for eight full months. Prior to the present invention, farmers would typically either round up their animals monthly to administer the medication, or would use a diffusion device which results in initially dangerously high drug exposures, followed by a prolonged period of sub-therapeutic levels as the drug diffusion device is depleted. Additionally, diffusion controlled devices are often problematic because the chemical structure and reactivity of the drug to be delivered can significantly impact the delivery curve.

The present invention offers the advantages of periodic administration of the drugs from a one time administration of the dosage form. The chemical structure of the drugs will have no effect on dosing because the microdelivery device 100 does not rely on drug diffusion or other drug-associated physicochemical phenomena to control the drug release pattern. Thus, considerable product development cost savings are achieved, in addition to improved drug efficacy.

Still another advantage of the method of the present invention is that the user can control when the microdelivery system 100 begins to administer the initial dose. A transmitter 170 can be provided to remotely transmit signals to the receiver and antenna 136. Signals from the transmitter 170 activate the timing circuit 132, thereby allowing the timing circuit to cause the drugs to be administered in a manner desired by the user. Thus, for example, a rancher could administer two microdelivery systems to each of his cattle, each of the microdelivery systems containing a six-month supply of antibiotics. One of the microdelivery systems would be activated to begin release of the antibiotics shortly after implantation. The other microdelivery system 100 could be activated approximately six months later by the transmitter 170. Thus, the rancher could reap the benefits of a one-year dosing regimen of antibiotics from a single administration of the dosage form. Annual administration of medication would save large amounts of time and money, by reducing animal handling and increasing the efficacy of the drugs. This method also provides a prolonged treatment period that can markedly exceed the duration of traditional diffusion devices, while eliminating concerns of host toxicity, subtherapeutic drug levels, development of parasite resistance, and tachyphylaxis.

The microdelivery system can be formed into numerous different embodiments. For example, in FIG. 3 there is shown a microdelivery system, generally indicated as 200, having an elongate tubular housing 204. Formed in the housing is a central compartment or vesicle 208, and a plurality of other vesicles 212 disposed in a circle about the central vesicle as shown. The vesicles 208 and 212 extend along a substantial length of the housing 204 generally in parallel with one another and include openings at the upper end 204a of the housing. A cover 216 with a plurality of rupturable portions 216a is disposed over the upper end 204a of the housing 204 to cover the openings of the vesicles, but to also rupture and allow discharge of the contents of a vesicle when adequate pressure is supplied to the cover from inside the vesicle. Although the vesicles 212 are shown to be generally the same size, different size and shape vesicles could be provided to allow for delivery of different amounts of a drug.

The housing 204 also includes a bottom compartment 220 in which are disposed a battery 224, an oscillator 228 and a timing circuit 232. The compartment 220 is separated from the vesicles 208 and 212 by a floor or substrate 236 in which are located a plurality of pyrotechnic gas generating beads 240. The circuit components 224, 228 and 232 selectively and successively ignite the pyrotechnic gas generating beads 240 in the same manner as discussed for the embodiment of FIG. 2.

Disposed in each vesicle 208 and 212 near the bottom thereof are pistons or plungers 244. The side surfaces of the plungers 244 are shaped to conform to and snugly fit within the side walls of the corresponding vesicles so that as a plunger is forced upwardly in a vesicle by gas pressure, it pushes out of the housing a drug formulation contained in the vesicle. The plungers 244 are forced upwardly in the corresponding vesicles by the activation of the pyrotechnic gas generating beads (or other geometric shapes) 240. Of course, the plungers 244 need not be used, as the drug formulation can be forced out the vesicle 208 by the gas itself.

Advantageously, the plungers 244 are made of polyurethane, synthetic rubber, silicone greases, petrolatym, paraffin, bees wax or other material which will allow for a slidably tight fit within the vesicles. The housing 204 could illustratively be made of rigid molded polymers (polycarbonate, ABS, polyesters, or other nonelastomeric thermoplastics or thermosets) or formed metals.

The microdelivery system 200 is advantageous in that the large number of vesicles 208 and 212 can hold numerous doses of the medications to be administered. For example, if alternating dosages are desired on a monthly basis, the microdelivery system 200 could provide drugs for more than a year without the need for implanting or otherwise administering additional dosage forms.

Figure 4:
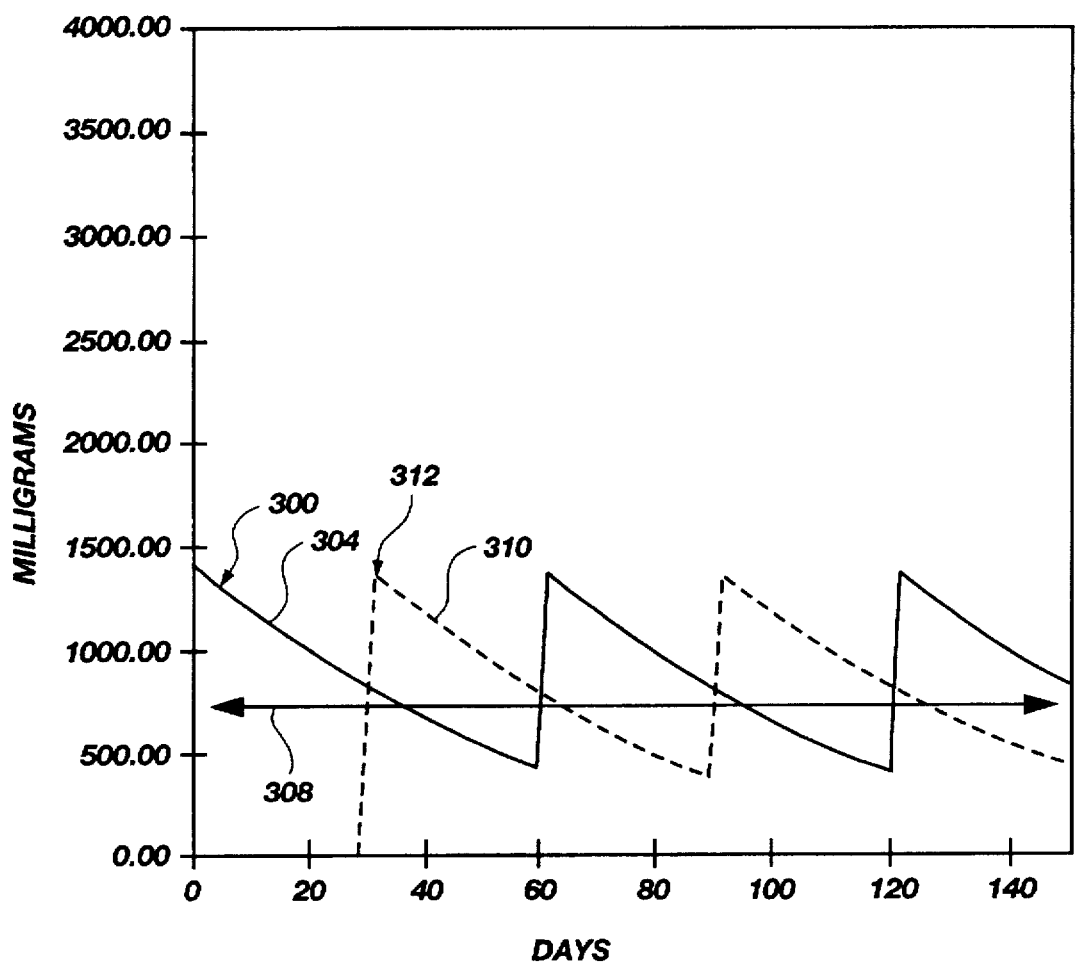
FIG. 4 shows a graph demonstrating a method of repetitive, alternating dosing in accordance with the principles of the present invention, along with a first-order kinetic decline for the delivery of each dose.

Referring now to FIG. 4, there is shown a graph demonstrating a method of dosing in accordance with the principles of the present invention, along with a first-order kinetic decline after delivery of each dose. For illustration purposes, the amount of drug available on an ear tag device configuration that is available to kill flies is graphed.

An initial dose 300 of a first drug, represented by solid line 304, is provided to kill flies. While referred herein as an ear tag which is clamped to an animal's ear, those skilled in the art will appreciate that the devices could be implanted, placed in the stomach of the animal, or placed in other areas. Additionally, the reference to a first drug should not be viewed as to limit the contents of a compartment of the microdelivery device, as two or more drugs could be disposed in a compartment of the microdelivery device for simultaneous administration.

As shown in FIG. 4, the initial dose is about 1400 milligrams. However, those skilled in the art will appreciate that the amount provided will depend both on the drug used, the type and size of the animal, and the disease. For illustration purposes, treatment of a parasitic fly infestation will be discussed, as those skilled in the art will be familiar with numerous parasiticides which may be used for such a purpose. After approximately 30 days, the levels of the first parasiticide 304 drop to near the efficacy threshold. Rather than providing additional quantities of the first drug 304, the microdelivery system (FIG. 2 or FIG. 3) is programmed to activate expulsion of a second drug 310 from a compartment or vesicle to provide the dosage indicated at 312. As shown in FIG. 4, 1400 milligrams of the second drug are provided to kill any parasites which have not been killed by the first drug 304.

As the second drug 310 falls toward the efficacy threshold 308, a sufficient quantity of the first drug 304 is again provided by the microdelivery system to bring the levels of the first drug 304 back up to 1400 milligrams. The amount of the first drug 304 necessary to reach the target dose is less than needed for the initial dose because of the residue first drug from the first dose. Thus, the second and subsequent dosings of either drug can typically be in smaller quantities, or delayed a sufficient period of time to prevent drug build up to levels which risk host toxicity. As shown in FIG. 4, approximately 900 milligrams is used for each dose after the initial dose for each drug.

By cycling the drugs in the manner described, considerable advantages are achieved. Of primary importance is that the cycling prevents the development of resistance to the parasiticide in the targeted parasite. There is always at least one of the drugs which is sufficiently above the efficacy threshold to eliminate the parasitic infestation. The two cycling drugs prevent multigenerational parasite turnover in the presence of subtherapeutic drug levels which is typically associated with development of resistance to drugs. Thus, resistance is substantially eliminated.

An additional advantage of the cycling is that the repetitive replenishment of drug keeps the total drug exposure for the host to a minimum. As shown in FIG. 4, one device administration has provided effective treatment of the animal for approximately five months. To achieve a similar treatment pattern with conventional dosage forms such as prior art diffusion devices would require the farmer, rancher, etc., to round up and treat the animal with the first or second drugs during each of the five months or periodically reapply diffusion-type devices. When dealing with large numbers of animals, the time and expense involved with such procedures is prohibitive.

Figure 4A:
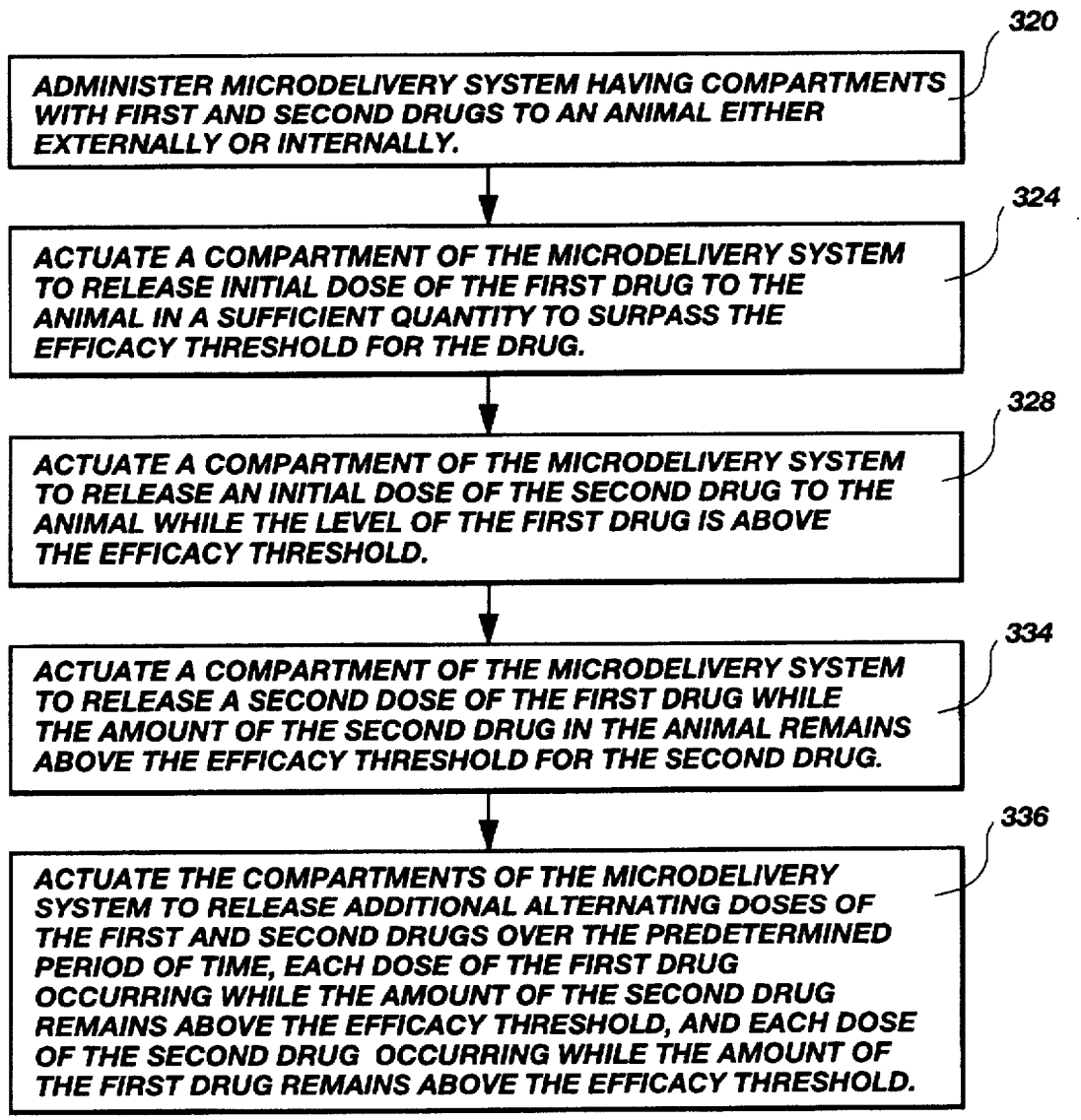
FIG. 4A shows a flow chart of the process used for implementing the dosing method demonstrated by the graph of FIG. 4.

FIG. 4A shows a flow chart of the process used for implementing the dosing method demonstrated by the graph of FIG. 4. The initial step 320 is accomplished by administering the device to the animal. The device may be attached to a collar, ear tag or similar device to provide topical treatments, or may be conveniently implanted, such as in an animal's ear or orally administered for retention in the rumen of ruminant animals, to provide the drugs into the blood stream.

The second step 324 is accomplished by providing an initial dose of the first drug in a sufficient quantity to surpass the efficacy threshold for the drug. This is followed by the third step 328 of providing an initial dose of the second drug while the level of the first drug is above the efficacy threshold.

The fourth step 332 is performed by supplying a second dose of the first drug while the amount of the second drug in the animal remains above the efficacy threshold for the second drug. Those skilled in the art will appreciate that the efficacy thresholds for the first and second drugs will often be different. However, for ease of reference, the efficacy thresholds for the two drugs are shown to be the same.

As indicated at 336, the dosing pattern can continue for a predetermined period of time, such as for 6 months. The actual time during which the microdelivery system will typically be used depends on the parasite infestation patterns and the amount of the first and second drugs which may be held in the microdelivery system.

While the graph of FIG. 4 shows the first and second drugs alternatingly falling below their efficacy thresholds, those skilled in the art will appreciate that a desirable dosing pattern is to keep both drugs above their efficacy thresholds for the entire period of treatment. Thus, instead of alternating the first and second drugs on a monthly basis, dosing may occur on a biweekly basis or a larger dose may be supplied. Such a dose, however, will be well below the potentially dangerous doses which attend administration of diffusion-type devices.

While more compartments are used if biweekly dosing is selected, the overall quantity of each drug used is relatively similar because the second and subsequent dose of each drug will need to be substantially less to bring the drug level to that shown at the top of each first-order kinetic curve.

EXAMPLE 1

In accordance with the graph and flow chart of FIGS. 4 and 4A, permethrin and chlorpyrifos insecticides are disposed in the microdelivery system 100 of FIGS. 2 and 2A and attached as an ear tag onto the ear of an animal for control of ectoparasites such as horn flies. The insecticides are formulated in combination with solvents, polymers and other additives as necessary to retard depletion of an expelled dose over a one-month period. A first dose of permethrin is supplied in sufficient quantity to raise the amount of available permethrin above the efficacy threshold. Applying a first-order kinetic depletion curve to the amount of permethrin that is available, the permethrin is formulated to stay above the efficacy threshold for one month. Similarly, the microdelivery system 100 is programmed to release a sufficient quantity of chlorpyrifos to bring the level of the drug above the efficacy threshold for chlorpyrifos and maintain a level above the efficacy threshold for one month. The microdelivery system 100 actuates a compartment holding the largest dose of chlorpyrifos four weeks after the first dose of permethrin is released.

Four weeks after the first dose of chlorpyrifos is released, the microdelivery system again actuates a compartment containing permethrin to release additional quantities of that drug. Because of the residual quantity of permethrin from the initial permethrin dose, the second permethrin dose will be a fraction of the first permethrin dose. According to FIG. 4, the second permethrin dose would be approximately 65% of the initial permethrin dose.

Therefore, the microdelivery system will be programmed as to which individual compartment to release for the first and all subsequent doses.

By continuing to alternate doses of the first and second drugs until each of the eight compartments 108 has been emptied, the microdelivery system 100 provides doses which prevent parasite infestations for approximately six months. This is accomplished with a single device administration, saving the farmer or rancher time and money, while allowing both drugs to be kept well below levels which might induce host toxicity. Additionally, tolerance development by the parasites is nearly eliminated because the continual replenishment and alternating of the pesticides precludes multigenerational parasite turnover under conditions of sub-lethal insecticide exposure that is required for tolerance to develop. It is important to recognize in accordance with the present invention that alternating, as used herein, may include a one to one sequence, e.g. A-B-A-B . . . ., or some other combination, e.g. A-A-B-A-A-B-A-B-B . . . ., as may be desired to most efficaciously minimize the threat of parasite, etc., infestation during a predetermined period of time, while minimizing the risk of toxicity to the animal.

Figure 5:
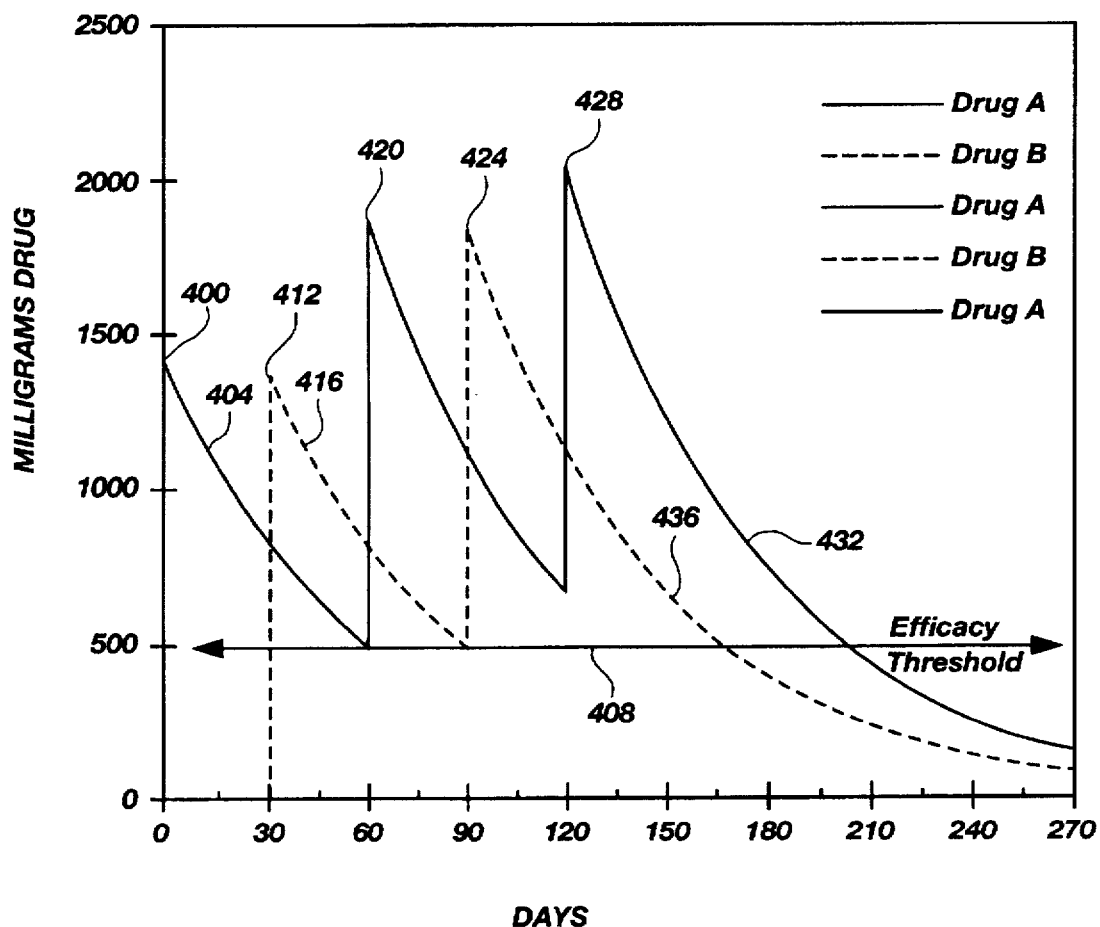
FIG. 5 shows graph of another dosing procedure in accordance with the present invention.

Referring now to FIG. 5, there is shown a graph of another dosing procedure in accordance with the present invention. An initial first dose 400 is provided of a first drug, the level of which is indicated by line 404. The initial first dose 400 of the first drug is approximately 1400 milligrams. At such a quantity, the amount of the first drug on the animal or available on a device configuration such as an ear tag, remains above the efficacy level 408 for approximately 60 days.

Approximately one month after the first drug is released, an initial dose 412 of a second drug, indicated by the dashed line 416, is released. The amount of the second drug 416 which is released is also 1400 milligrams and will take approximately 60 days to drop below the efficacy threshold for the second drug. For ease of reference, the efficacy threshold for the second drug is indicated as being the same as the efficacy threshold 208 for the first drug. Those skilled in the art will appreciate that the efficacy threshold for each drug used must be considered when determining the quantity of that drug released and the time between dosing and the presence of subtherapeutic levels of the drug.

Unlike the dosing regimen in FIG. 4, the amount of drug delivered with each dose is kept the same. Thus, because the level of the first drug has fallen to 500 milligrams, providing a second dose of 1400 milligrams, as indicated at 220, results in 1900 milligrams of therapeutically available drug. Likewise, a similar increase in the level of the second drug is achieved by use of a full 1400 milligram dose of the second drug, indicated at 424.

FIG. 5 also shows a third dose, indicated at 428, of the first drug. The third dose 428 is also 1400 milligrams, thereby bringing the amount of the first drug to a peak of slightly more than 2000 milligrams. Each of the two drugs are eliminated or degraded with a first-order kinetic decline, as indicated at 432 for the first drug and 436 for the second drug.

The dosing of the drugs so as to create an increase in the drug level in the animal with each subsequent dose can be used advantageously in several ways. First, if the goal is simplicity in manufacturing the microdelivery system, the method allows the system to be manufactured with each compartment containing the first drug to have the same quantity. Likewise, each compartment containing the second drug can have the same quantity. Rather than requiring the microdelivery system 100 or 200 to be programmed to release the compartment with the first (higher) dose of each drug, the system must only ensure that the compartments containing the first and second drugs, respectively, are released in an alternating pattern. To prevent build-up of the first and second drugs, all doses after the second dose for each drug would simply be delayed.

In the alternative, the escalating quantity achieved by the dosing level as shown in FIG. 5 can be used to improve the correlation between dosing and infestation patterns. For example, if a particular parasite infestation is most common during a specific month or period, the microdelivery system can be programmed to release a compartment containing a particularly high quantity of one or both drugs during the infestation period. Doses subsequent to the infestation period would be modified to return the drugs to a level desired when high-level infestation is not a concern.

Of course, a single drug could be used in the dosing pattern. As will be apparent to those skilled in the art from FIG. 5, either of the drugs delivered could be administered periodically to keep the drug doses to a minimum while ensuring that the available amount of the drug remains above the efficacy threshold. In such a manner, the development of resistance would be greatly diminished, as the available amount of the drug remains above the subtherapeutic level needed for resistance to develop.

Figure 3:
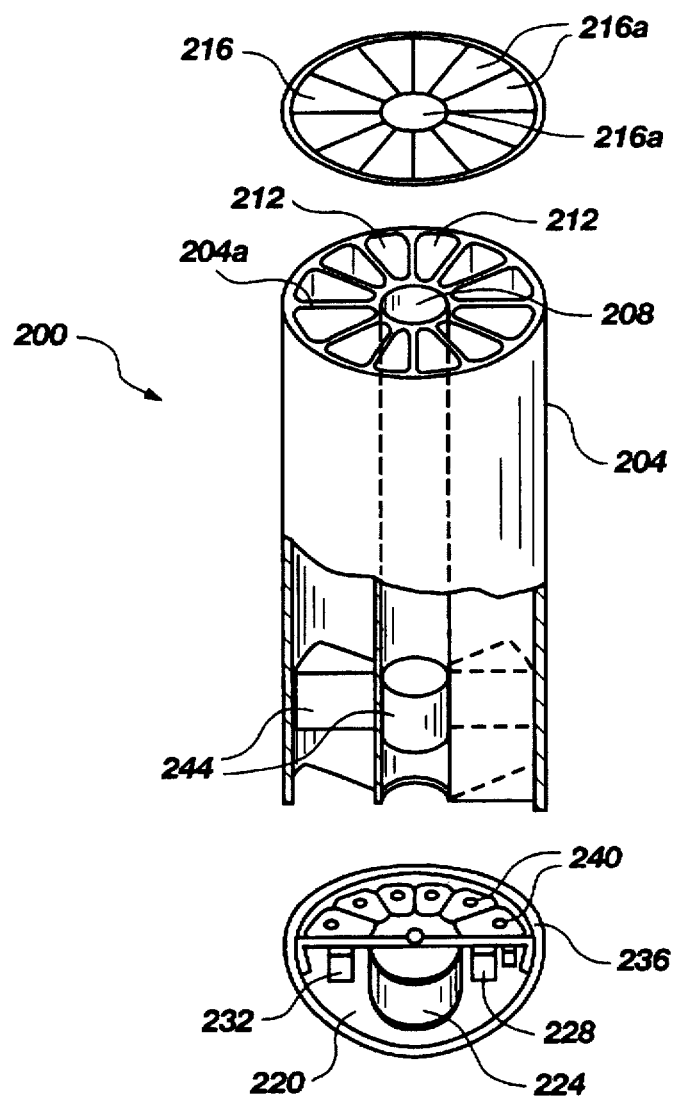
FIG. 3 shows an isometric, exploded, partially cutaway view of an alternate embodiment of a microdelivery system which may be used in accordance with the teachings of the present invention.
Figure 5A:
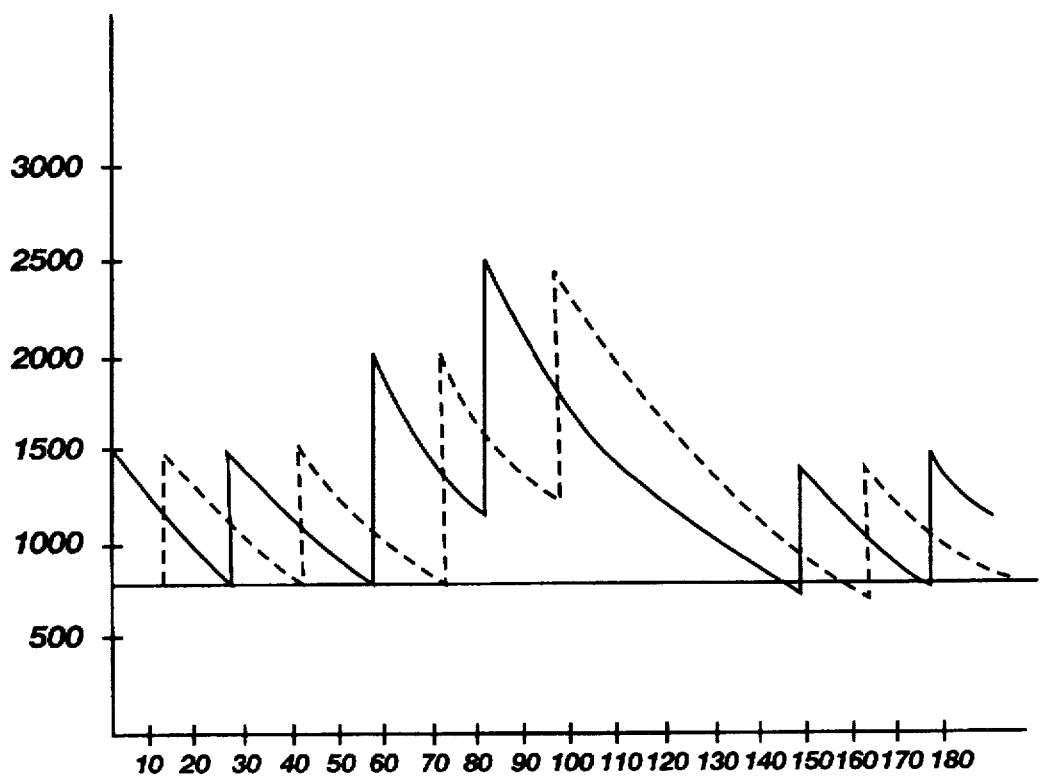
FIG. 5A shows another graph of a dosing procedure performed in accordance with the present invention.

Referring now to FIG. 5A, there is shown a graph representing the use of a microdelivery device such as those shown in FIGS. 2 through 3. The device is used to selectively control the therapeutically available amount of each drug to correlate the same to an infestation period, indicated at 504. An initial dose 508 of a first drug, indicated by the solid line 512 is 1400 milligrams and the efficacy threshold 514 for the first drug is 700 milligrams. Thus, the first drug 508 falls to the efficacy threshold 514 after approximately 30 days.

A second drug, indicated by dashed line 516 is provided. The initial dose 520 is 1400 milligrams and the second drug 516 has a similar efficacy threshold 514 as the first drug. The initial dose 520 of the second drug 516 is provided approximately 15 days after the initial dose 508 of the first drug 512.

A second dose 524 of the first drug 512 is provided after thirty days. To achieve an available level of 1400 milligrams for the first drug 512, the second dose 324 is 700 milligrams.

On about the forty-fifth day, a second dose 528 of the second drug 516 is provided. The second dose 528 of the second drug 516 is also 700 milligrams, thereby bringing the available level of the second drug back up to approximately 1400 milligrams.

A third dose 532 of the first drug 512 is provided on the 60th day. Because the 60th day is also the approximate beginning of the typical infestation period 504 for a particular parasite, the third dose 532 of the first drug 512 is increased to 1400 milligrams, the same as the initial dose 308. The third dose of the first drug 512 achieves a level of approximately 2100 milligrams. The increase in drug level decreases the risk that the animal will become infested during a high-level infestation period.

The second drug 516 is also released in a greater amount during its third dose 536 to raise its level to approximately 2100 milligrams. The level for each of the drugs is raised up to approximately 2450 milligrams by providing a 1400 milligram fourth dose 540 and 544 for the first and second drugs, respectively.

To return to the preinfestation drug levels, the fifth dose 350 and 354, for each of the drugs is spaced approximately 60 days from the fourth doses 540 and 544 of the respective drug. It is important to note that while the first drug transiently falls below the efficacy threshold, the second drug remains fully therapeutic and covers the need. The fifth dose 550 for first drug 512 is 790 milligrams, as is the fifth dose 554 for the second drug 516. Any subsequent treatment is provided by doses of 700 milligrams.

Thus it can be seen that the method for using the microdelivery system 100 or 200 enables the user to control dosing patterns to correlate available drug levels with infestation patterns. By careful planning, the user is able to use the minimum amount of the drug to maximize efficacy. This can be achieved either by timing the release of each compartment to achieve desired dosing levels, or by adjusting the quantity of the first or second drug which is contained in each compartment and then actuating the delivery from the compartments in a predetermined pattern. When a first quantity of one of the drugs is delivered in the initial dose, maintaining the effective levels of the drug can either be done by applying a second, smaller quantity on the second and subsequent dose for that drug, or by providing the same dose and extending the time before the next delivery. Likewise, the delivered drug levels can be modulated to correspond with seasonal fluctuations in parasitic infestations by altering either the quantity of the drugs delivered and/or by changing the timing at which the drugs are delivered.

While discussed primarily with respect to the control of parasites in animals, those skilled in the art will appreciate that the present method has a variety of medical applications. Thus, for example, a microdelivery device 100 or 200 could be programmed to provide medications in patterns which maximize their efficacy while minimizing adverse reactions or other problems. Furthermore, because the microdelivery devices are implantable or attachable to the patient, the drugs may be delivered in the most efficacious cycling while allowing the patient relative mobility. Thus, the principles of the present invention are equally applicable to medical applications in humans as it is to parasite control in animals.

Figure 6:
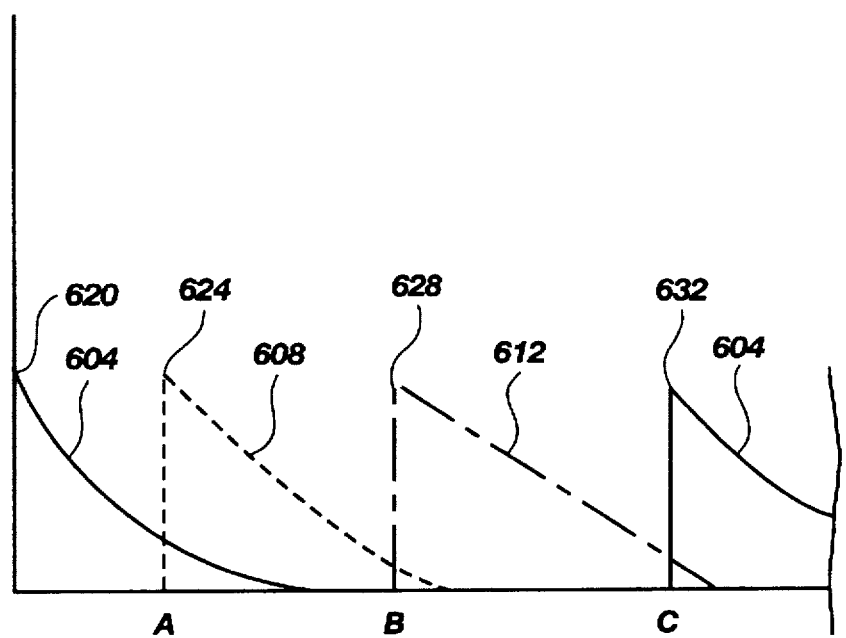
FIG. 6 shows a graph of yet another dosing procedure performed in accordance with the present invention.

Referring now to FIG. 6, there is shown an alternate dosing procedure of the present invention. Each of three drugs 604, 608 and 612 are provided to an animal. However, if two or more of the drugs are simultaneously present in sufficient quantities, the animal being treated will suffer from adverse side effects. Those skilled in the art will appreciate that the type and extent of any side effects are dependant on the amount of drugs provided.

To prevent adverse side effects, the first drug 604 is supplied to the animal in an initial dose 620. Based on the dose provided, it is known that the systemic level of the first drug 604 will fall to a level at which the second drug 608 may be introduced without side effects after time period A. Thus, the microdelivery system 100 (FIGS. 2 and 2A) or 200 (FIG. 3) is programmed to release an initial dose 624 of the second drug 608 after time period A.

Following a first-order kinetic curve, the second drug 608 falls to a sufficiently low level after time period B to allow introduction of an initial dose 628 of the third drug 612. The third drug 612 also is eliminated until a second dose 632 of the first drug 604 may be introduced at time period C. The alternate dosing of the first, second, and third drugs 604, 608 and 612, respectively, can be continued until the drug delivery is no longer needed, or until the microdelivery system 100 or 200 has been fully depleted.

Those skilled in the art will appreciate that regardless of which microdelivery system is used, the practitioner responsible for assuring that drug therapy is provided can utilize established pharmacokinetic/pharmacodynamic principles and program the devices to deliver an optimal dosing regimen. Relying on this information, the programmer can determine not only when a drug should be released, he or she can selectively control compartments having different dosing levels to select an optimum dosing pattern for the particular use.

While the present invention will be desirable for a large number of insecticides, parasiticides and other drugs as listed in the Merck Index, the following drugs are currently viewed as being highly desirable for administration in accordance with the principles of the present invention which are set forth above:

chlorpyrifos diazinon permethrin lambdacyhalothrin pyrimiphos methyl ivermectin doramectin moxidectin and insect growth regulators Thus there is disclosed a method for automatic, alternate dosing of two or more drugs. Those skilled in the art will recognize numerous modifications which can be made without departing from the scope and spirit of the invention. The appended claims are intended to cover the scope of the invention.

What is claimed is:

1. A method for automatic delivery of one or more drugs, the method comprising:
   a) selecting a microdelivery system having a plurality of compartments disposed therein for holding a plurality of doses of at least a first drug to be administered to an animal/human;
   b) administering the microdelivery system to the animal/human;
   c) actuating the microdelivery system to provide an initial dose of the first drug from at least one compartment of the microdelivery system to the animal/human in sufficient quantity to exceed the efficacy threshold for the first drug in the animal/human; and
   d) actuating the microdelivery system to provide a second dose of the first drug from at least one compartment of the microdelivery system to the animal/human at a predetermined time after the initial dose of the first drug and while the drug supplied by the initial dose remains above the efficacy threshold.

2. The method of claim 1, wherein step (a) comprises, more specifically, selecting a microdelivery system having a second drug disposed in at least one of the plurality of compartments, and wherein the method further comprises;
   (e) actuating the microdelivery system to provide an initial dose of the second drug at a predetermined time after the initial dose of the first drug.

3. The method of claim 2, wherein the method further comprises selectively actuating the microdelivery system to provide alternating doses of the first and second drugs in a predetermined pattern.

4. The method of claim 2, wherein the method comprises, more specifically, providing at least two doses of the first drug before the initial dose of the second drug.

5. The method of claim 2, wherein step (a) comprises, more specifically, selecting a microdelivery system having a third drug disposed in at least one of the plurality of compartments, and wherein the method further comprises;
   (f) actuating the microdelivery system to provide an initial dose of the third drug at a predetermined time after the initial dose of the first drug.

6. The method of claim 5, wherein the method further comprises actuating the microdelivery system in a pattern to provide alternating doses of the first, second and third drugs.

7. The method of claim 1 wherein step (b) comprises, more specifically, attaching the microdelivery system to the animal/human such that step (c) provides a topical application.

8. The method of claim 1, wherein step (b) comprises, more specifically, disposing the microdelivery system into the rumen of a ruminant animal.

9. The method of claim 1, wherein step (b) comprises, more specifically, implanting the microdelivery system into the animal/human.

10. The method of claim 1, wherein step (c) comprises, actuating a plurality of compartments to provide the initial dose of the first drug.

11. The method according to claim 1, wherein the first drug is selected from the group consisting of permethrin, chlorpyrifos, diazinon, lambdacyhalothrin, pyrimiphos methyl, ivermectin, doramectin, moxidectin and insect growth regulators.

12. The method according to claim 1, wherein the method comprises, more specifically, disposing a dose in one of the compartments which is a mixture of a first drug and a second drug.

13. A method for automatic alternate dosing of at least two drugs in an animal, the method comprising:
   a) selecting a microdelivery system having a plurality of compartments disposed therein for holding at least a first drug and a second drug;
   b) administering the microdelivery system to the animal;
   c) actuating the microdelivery system to provide an initial dose of the first drug from a compartment of the microdelivery system to the animal; and
   d) actuating the microdelivery system to provide an initial dose of the second drug from a compartment of the microdelivery system to the animal at a predetermined time after the initial dose of the first drug.

14. The method of claim 13, further comprising:
   e) actuating the microdelivery system to provide a second dose of the first drug at a second predetermined time after the initial dose of the second drug.

15. The method of claim 14, further comprising:
   f) actuating the microdelivery system to provide a second dose of the second drug at a third predetermined time after the second dose of the first drug.

16. The method of claim 15, wherein the method further comprises delivering additional doses of the first and second drugs in an alternating pattern, each dose being spaced a predetermined period of time.

17. The method of claim 13, wherein the method comprises, more specifically, delivering a second dose of the first drug prior to the initial dose of the second drug.

18. The method of claim 13, wherein step (a) comprises, more specifically, selecting a microdelivery system having compartments for storing first, second and third drugs.

19. The method according to claim 18, wherein the method further comprises:
   e) actuating the microdelivery system to provide an initial dose of the third drug at a third predetermined time after the initial dose of the second drug.

20. The method according to claim 19, further comprising:
   f) actuating the microdelivery system to provide a second dose of the second drug at a fourth predetermined time after the second dose of the first drug.

21. The method of claim 20, wherein the method further comprises delivering additional doses of the first and second drugs in an alternating pattern, each dose being delivered at a predetermined period of time subsequent to a prior dose.

22. The method of claim 13, wherein the step (a) comprises, more specifically, providing one of the compartments with a first quantity of the first drug and providing a plurality of the remaining compartments with a second quantity of the first drug which is less than the first quantity.

23. The method of claim 22, wherein the method further comprises releasing the compartments having the second quantity of the first drug at intervals sufficiently distant from one another so that the amount of the first drug available to the animal is substantially the same immediately after each dose of the first drug as the first quantity.

24. The method of claim 22, wherein step (a) further comprises, providing one of the compartments with a first quantity of the second drug and providing a plurality of the remaining compartments with a second quantity of the second drug which is less than the first quantity.

25. The method of claim 22, wherein step (a) further comprises, providing one of the compartments with a first quantity of the second drug and providing a plurality of the remaining compartments with a second quantity of the second drug which is greater than the first quantity.

26. The method of claim 13, wherein the step (a) comprises, more specifically, providing one of the compartments with a first quantity of the first drug and providing a plurality of the remaining compartments with a second quantity of the first drug which is greater than the first quantity.

27. The method of claim 26, wherein step (a) further comprises, providing one of the compartments with a first quantity of the second drug and providing a plurality of the remaining compartments with a second quantity of the second drug which is greater than the first quantity.

28. The method of claim 13, wherein step (a) comprises, more specifically, providing different quantities of the first and second drugs in the compartments, and wherein the method further comprises, selectively releasing the compartments to obtain a desired level of the first and second drugs within the animal.

29. The method of claim 13, wherein the method further comprises controlling the quantity of the first and second drugs within the animal by selectively controlling when each compartment releases the drug contained therein.

30. The method of claim 13, wherein steps (c) and (d) result in available levels of the first and second drugs to the animal, and wherein the method further comprises, delivering additional doses of the first and second drugs in such a manner to increase the levels of the drugs during seasonal parasite infestations.

31. The method of claim 13, wherein step (b) comprises, more specifically, implanting the microdelivery system within the animal.

32. The method of claim 13, wherein step (b) comprises, more specifically, topically attaching the microdelivery system to the animal.

33. The method of claim 13, wherein step (b) comprises, more specifically, disposing the microdelivery system within the stomach of the animal.

34. The method of claim 13, wherein the first drug is selected from the group consisting essentially of permethrin, chlorpyrifos, diazinon, permethrin, chlorpyrifos, diazinon, lambdacyhalothrin, pyrimiphos methyl, ivermectin, doramectin, and moxidectin.

35. The method of claim 34, wherein the second drug is selected from the group consisting essentially of permethrin, chlorpyrifos, diazinon, lambdacyhalothrin, pyrimiphos methyl, ivermectin, doramectin, and moxidectin.

36. A method for automatic alternate dosing of at least two drugs in an animal/human, each of the drugs having an efficacy threshold level for the animal/human, the method comprising:
   a) selecting a microdelivery system having at least two compartments for holding at least first and second drugs;
   b) administering the microdelivery system to the animal/human;
   c) releasing a first dose of the first drug from the microdelivery system in sufficient quantity to exceed the efficacy threshold for the first drug for the animal/human; and
   d) releasing a first dose of the second drug from the microdelivery system in sufficient quantity to exceed the efficacy threshold of the second drug for the animal/human, while the level of the first drug remains above the efficacy threshold for the first drug.

37. The method for alternate dosing of at least two drugs of claim 36, wherein the method further comprises:
   e) releasing a second dose of the first drug from the microdelivery system in sufficient quantity so that the total quantity of the first drug administered to the animal/human exceeds the efficacy threshold for the first drug while the level of the second drug remains above the efficacy threshold for the second drug.

38. The method for alternate dosing of at least two drugs of claim 37, wherein the method further comprises:
   f) releasing a second dose of the second drug from the microdelivery system in sufficient quantity so that the total quantity of the second drug administered to the animal/human exceeds the efficacy threshold for the second drug while the level of the first drug remains above the efficacy threshold for the first drug.

39. The method for alternate dosing of at least two drugs of claim 38, wherein the second dose of the first drug is released while the level of the first drug administered to the animal/human remains above the efficacy threshold for the first drug.

40. The method for alternate dosing of at least two drugs of claim 38, wherein the second dose of the second drug is released while the level of the second drug remains above the efficacy threshold for the second drug.

41. The method for alternate dosing of at least two drugs of claim 36, wherein step (a) comprises, more specifically, selecting a microdelivery system having at least two compartments for holding at least first and second drugs, and a circuit programmed to release the first and second drugs at predetermined intervals.

42. The method for alternate dosing of at least two drugs of claim 41, further comprising programming the microdelivery system to release an initial dose of the first drug in sufficient quantity that the first drug provided to the animal/human will remain at a level exceeding the efficacy threshold for the first drug until the second drug is released.

43. The method for alternate dosing of at least two drugs of claim 36, wherein step (a) comprises, more specifically, selecting a microdelivery system having a plurality of compartments therein, each compartment holding a single dose of one of the first and second drugs.

44. The method for alternate dosing of at least two drugs of claim 43. wherein the method further comprises selectively actuating the compartments to alternatingly release doses of the first and second drugs until all of the compartments holding the first and second drugs have been actuated.

45. The method for alternate dosing of at least two drugs of claim 36. wherein step (b) comprises attaching the microdelivery system to the animal/human so as to provide topical delivery when a dose is released.

46. The method for alternate dosing of at least two drugs of claim 36. wherein step (b) comprises disposing the microdelivery system in the rumen of an animal.

47. The method for alternate dosing of at least two drugs of claim 36. wherein step (b) comprises implanting the microdelivery system to the animal/human so as to provide internal delivery when a dose is released.

48. The method for alternate dosing of at least two drugs of claim 36. wherein step (b) comprises selecting a microdelivery system having at least compartment containing a hormone, and wherein the method comprises actuating said at least one compartment subsequent to the initial dose of the first drug.

49. The method for alternate dosing of at least two drugs of claim 36. wherein the method further comprises remotely activating the microdelivery system.

50. The method of claim 36. wherein the first drug is selected from the group consisting essentially of permethrin, chlorpyrifos, diazinon, lambdacyhalothrin, pyrimiphos methyl, ivermectin, doramectin, and moxidectin.

51. The method of claim 50. wherein the second drug is selected from the group consisting essentially of permethrin, chlorpyrifos, diazinon, lambdacyhalothrin, pyrimiphos methyl, ivermectin, doramectin, and moxidectin.

52. The method of claim 36. wherein the first drug is selected from the group consisting essentially of insect growth regulators.

53. The method of claim 52. wherein the second drug is selected from the group consisting essentially of insect growth regulators.

* * * * *